United States Patent
Basedow et al.

(10) Patent No.: US 6,198,017 B1
(45) Date of Patent: Mar. 6, 2001

(54) MEDICAL PRESSURE-SENSITIVE ADHESIVES WITH HIGH PERMEABILITY TO WATER VAPOR AND HIGH ADHESIVE FORCE, AND PLASTERS PROVIDED THEREWITH

(75) Inventors: Arno Basedow, Bad Vilbel; Frank Kura, Meerbusch; Kurt Seeger, Neuweid, all of (DE)

(73) Assignee: Lohmann GmbH & Co. KG, Neuwied (DE)

( * ) Notice: Subject to any disclaimer, the term of this patent is extended or adjusted under 35 U.S.C. 154(b) by 0 days.

(21) Appl. No.: 09/214,856
(22) PCT Filed: Jun. 28, 1997
(86) PCT No.: PCT/EP97/03392
§ 371 Date: Mar. 1, 1999
§ 102(e) Date: Mar. 1, 1999
(87) PCT Pub. No.: WO98/03208
PCT Pub. Date: Jan. 29, 1998

(30) Foreign Application Priority Data

Jul. 18, 1996 (DE) ............................... 196 28 999

(51) Int. Cl.$^7$ .................................... A61F 13/00
(52) U.S. Cl. ................ 602/52; 602/44; 602/45; 602/59
(58) Field of Search .................. 602/43, 41–42, 602/44–46, 48–49, 53, 58–60, 75

(56) References Cited

U.S. PATENT DOCUMENTS

| 4,420,470 | * | 12/1983 | Otsuka et al. . | |
|---|---|---|---|---|
| 4,994,267 | * | 2/1991 | Sablotsky . | |
| 5,785,985 | | 7/1998 | Czech et al. | 424/448 |

FOREIGN PATENT DOCUMENTS

| 41 26 230A | 2/1993 | (DE) . |
|---|---|---|
| 44 16 928 C1 | 5/1994 | (DE) . |
| 0 387 751 A2 | 12/1990 | (EP) . |
| 0 701 822 A2 | 9/1995 | (EP) . |
| WO 84/03937 | 10/1984 | (WO) . |

* cited by examiner

Primary Examiner—Michael A. Brown
Assistant Examiner—Lalita M. Hamilton
(74) Attorney, Agent, or Firm—Law Offices of Jane Massey Licata

(57) ABSTRACT

Medicinal pressure-sensitive adhesives, adhering to both dry and wet skin, characterized by a mixture of
a) 20–50 wt-% of a hydrophilic (meth)acrylate copolymerizate containing tertiary amino groups,
b) 20–50 wt-% of a hydrophobic (meth)acrylate copolymerizate containing carboxyl groups,
c) 10–40 wt-% of one or more mono- or dicarboxylic acids,
d) 0–10 wt-% of a polyol, and
e) 0.02–0.5 wt-% of a cross-linking system reacting with at least one copolymerizate,
whereby the sum of components a to e equals 100 wt-%, with a water-vapor permeability of $\geq 30,000$ $g \cdot m^{-2} \cdot 24$ $h^{-1}$, measured on a pressure-sensitive adhesive film with a thickness of 40 $\mu m$.

15 Claims, No Drawings

MEDICAL PRESSURE-SENSITIVE ADHESIVES WITH HIGH PERMEABILITY TO WATER VAPOR AND HIGH ADHESIVE FORCE, AND PLASTERS PROVIDED THEREWITH

The invention relates to medicinal pressure-sensitive adhesives which adhere to both dry and wet skin, and to plasters provided with said adhesives.

The present invention especially relates to medicinal pressure-sensitive adhesives with excellent adhesion and with a water-vapor permeability (WVP) of at least 30,000 $g \cdot m^{-2} \cdot 24\ h^{-1}$ (measured on a pressure-sensitive adhesive film with a weight of 40 $g/m^2$) and to their use for the production of pressure-sensitive adhesive medical products, e.g. for emergency or sports medicine.

The term pressure-sensitive adhesive here denominates adhesives which adhere reversibly to the respective surface through exertion of pressure.

The water-vapor permeability is the amount of water which escapes from an inverted cup—sealed with the substrate and filled with water—through the substrate to be measured per area and time at an ambient climate of 40° C. and 20% relative humidity.

DE-OS 44 16 928 teaches wet adhesives on the basis of acrylate copolymers. Further components are emulsifiers containing quaternary ammonium groups, emulsifiers containing polyoxyalkylenes, polyvinyl carboxylic acid, tackifying resins and cross-linking agents. The disadvantages of the products manufactured according to this document are on the one hand that the adhesives only adhere well to moist skin if the skin is dried before application, and on the other hand that the emulsifiers containing quaternary ammonium groups are not cross-linked with the polymer backbone, so that they can be dissolved out in damp surroundings and have a cytotoxic effect. Also, the water-vapor permeability of 30,000 $g \cdot m^{-2} \cdot 24\ h^{-1}$ described in said document, measured on a pressure-sensitive adhesive film with a weight of 30 $g/m^2$, is in many cases insufficient.

EP 0 415 055 describes pressure-sensitive adhesives with the water-soluble salt of an uncrosslinked copolymer of an amino group-containing monomer and at least one alkyl (meth)acrylate.

The disadvantages of this adhesive are on the one hand that the adhesive characteristics of the thus produced adhesive depend very strongly on the residual moisture content, thus making a complicated controlling of the drying conditions necessary, and on the other hand that the adhesive has absorbed so much moisture after a longer wearing period that when the carrier material is pulled off of the skin, the adhesive completely remains on the skin and must be removed with much effort using a soap solution.

It is thus the object of the present invention to provide medicinal pressure-sensitive adhesives which adhere excellently to dry, moist and wet skin and at the same time avoid the above mentioned disadvantages such as the necessity of pre-drying the skin, cytotoxic components and adhesive residue upon removal, and which are also suited for longer wearing periods due to their high WVP of at least 30,000 $g \cdot m^{-2} \cdot 24\ h^{-1}$ 30,000 $g \cdot m^{-2} \cdot 24\ h^{-1}$, at a pressure-sensitive adhesive film weight of 40 $g/m^2$.

These surprisingly good characteristics are achieved in the adhesive according to the present invention which is characterized by a mixture of
a) 20–50 wt-% of a hydrophilic (meth)acrylate copolymerizate containing tertiary amino groups,
b) 20–50 wt-% of a hydrophobic (meth)acrylate copolymerizate containing carboxyl groups,
c) 10–40 wt-% of one or more mono- or dicarboxylic acids,
d) 0–10 wt-% of a polyol, and
e) 0.02–0.5 wt-% of a cross-linking system reacting with at least one copolymerizate,
whereby the sum of components a to e equals 100 wt-%, with a water-vapor permeability of $\geq 30,000\ g \cdot m^{-2} \cdot 24\ h^{-1}$, measured on a pressure-sensitive adhesive film with a thickness of 40 $\mu m$.

The pressure-sensitive adhesive according to the invention adheres excellently to both dry and sweaty skin, it can be removed from the skin without residue, and it has such a high WVP that it enables a longer wearing period even in damp surroundings.

Eudragit® E 100 (Röhm Pharma) is an example for a hydrophilic methacrylate copolymerizate containing tertiary amino groups.

Durotak® 1050 (National Starch & Chemical) is an example for a hydrophobic acrylate copolymer containing carboxyl groups. Suitable carboxylic acids are lauric, myristic or palmitic acid, and suitable dicarboxylic acids are adipic, octanedioic or sebacic acid.

Glycerin is a polyol according to the invention.

Cross-linking agents are e.g. metal chelates, metal acid esters, polyisocyanates, epoxide resins, aziridine resins, and triazine resins.

A further object of the invention is the use of the pressure-sensitive adhesives according to the invention for the production of pressure-sensitive adhesive medical products e.g. for emergency, intensive care and sports medicine, and also for occlusive dressings such as e.g. transdermal systems. If necessary, the medical products can be sterilized by water vapor, y-irradiation or gassing with ethylene oxide.

The thus obtained pressure-sensitive adhesives were evaluated—coated onto polyurethane films with good breathing properties—by means of physical-technical tests such as WVP (the water-vapor permeability of the pressure-sensitive adhesive film is calculated according to the following formula:

$$\frac{1}{WVP_{total}} = \frac{1}{WVP_{polyurethane\ film}} + \frac{1}{WVP_{adhesive})}$$

and testing of the adhesive strength on steel plates according to AFERA 4001 as well on a skin model of polyurethane. With this skin model, an adhesive strength is achieved which is, on average, approximately 2N/25 mm higher than the corresponding average value on human skin. This is valid basically regardless of whether the pressure-sensitive adhesive is based on natural or synthetic rubber, a solvent- or water-based acrylate copolymer, or a silicon.

The samples were further tested on the skin of twenty test persons following a given evaluation system by means of statistical analysis. Strips of 2.5 cm×5 cm were applied to the hairless inner section of the forearms (dry), and pieces of 3 cm×3 cm were applied to the freshly washed and dried (moist) and undried (wet) palms of the test persons. Apart from the subjective evaluation of the adhesive strength after 1 hour and after 24 hours, further evaluation criteria were the dermatological acceptability and a pain-free, residue-free removal. The statistical analysis of these tests, whereby a standard was always set at 100%, led to the result that products with the pressure-sensitive adhesives according to the invention adhere to dry and wet skin without problem, do not cause skin irritations, and can be removed practically without residue.

In the following, the present invention is described in more detail with the help of the following examples:

EXAMPLE 1

200 g of ethyl acetate are placed into a 1 l reaction vessel with a stirrer, drip funnel, reflux cooler and gas supply nozzles, and heated to 80° C. Within a time span of 50 minutes, a monomer mixture of 80 g of n-butyl acrylate, 80 g of ADAME (Elf Atochem), 40 g of methacrylic acid, and 0.5 g of VAZO 64 (Du Pont) is added dropwise under stirring. After a further 6 hours and cooling to 60° C., 60 g of ethyl acetate and 40 g of isopropanol, together with 120 g of lauric acid and 22 g of adipic acid, are added to this copolymerizate A. After cooling to room temperature, 20 g of glycerin and 340 g of a copolymerizate B, polymerized as described above from 200 g of n-butyl acrylate, 275 g of 2-ethylhexyl acrylate, 25 g of acrylic acid, and 2.5 g of VAZO 64 in 500 g of ethyl acetate, are admixed to the homogenous mixture. Furthermore, 100 g of a 2.5% aluminum acetylacetonate (AlAcA) solution are added for crosslinking.

The thus obtained pressure-sensitive adhesive is coated onto a siliconized polyester film in different layer thicknesses with a spreading knife and dried for 30 minutes at 80° C. in a vent air drying cabinet, resulting in pressure-sensitive adhesive films with a thickness of 25 $\mu$m, 45 $\mu$m and 60 $\mu$m (referred to as a, b and c). The pressure-sensitive adhesive films are transfer laminated onto a polyurethane film with a thickness of 25 $\mu$m and a WVP of 40,000 g·m$^{-2}$·24 h$^{-1}$. The evaluation (see Table 1) was carried out in comparison to a standard commercial product composed of a pressure-sensitive adhesive film with a thickness of 30 $\mu$m and a polyurethane film with a thickness of 25 $\mu$m.

TABLE 1

| | Unit | Standard | a) | b) | c) |
|---|---|---|---|---|---|
| Thickness of the polyurethane film | $\mu$m | 25 | 25 | 25 | 25 |
| Thickness of the adhesive film | $\mu$m | 30 | 25 | 45 | 60 |
| WVP$_{\text{pressure-sensitive adhesive film, inverted cup}}$ | g·m$^{-2}$·24 h$^{-1}$ | 5000 | 62100 | 49300 | 38400 |
| Adhesive strength AFERA 4001 | N/25 mm | 7.5 | 4.0 | 5.2 | 6.1 |
| Adhesive strength polyurethane skin model subjective evaluation, normed at a standard of 100% | N/25 mm | 3.6 | 6.2 | 6.5 | 6.9 |
| dry | % | 100.0 | 99.8 | 102.9 | 105.2 |
| moist | % | 100.0 | 130.2 | 153.0 | 142.8 |
| wet | % | 100.0*[1] | 180.2 | 210.7 | 254.8 |

*[1]: very weak adhesion or no adhesion at all

In comparison with the standard, an almost equal level of adhesive strength can be observed in the measurement on dry skin (under normal ambient conditions).

In the measurement on moist skin and especially on wet skin, the excellent performance of the new pressure-sensitive adhesive becomes apparent. Whereas the standard product does not adhere to the wet skin of most of the test persons, the pressure-sensitive adhesive according to the invention continues to achieve a sufficient adhesive strength.

EXAMPLES 2–5

The following mixtures were processed analogously to Example 1 (the given values apply to the respective solid materials) and coated so as to achieve a pressure-sensitive adhesive film of the determined thickness:

| | Example 2 | Example 3 | Example 4 | Example 5 |
|---|---|---|---|---|
| hydrophilic copolymer | 240 g of copolymer A | 140 g of copolymer A | 186 g of Eudragit E 100 (Röhm Pharma) | 183 g of Eudragit E 100 (Röhm Pharma) |
| hydrophobic copolymer | 127 g of copolymer B | 140 g of Durotak 1050 (National Starch) | 167 g of copolymer B | 211 g of Durotak 1050 (National Starch) |
| fatty acid | 99 g of lauric acid | 140 g of myristic acid | 112 g of lauric acid | 183 g of myristic acid |
| dicarboxylic acid | 17 g of octanedioic acid | 35 g of sebacic acid | 20 g of adipic acid | 14 g of octanedioic acid |
| polyol | 14 g of glycerin | 14 g of glycerin | 13 g of glycerin | — |
| crosslinking agent | 2.1 g of AlAcA | 0.7 g of AlAcA | 1.5 g of CX-100*[1] | 1.4 g of PBT*[2] |
| solid material | 35% | 40% | 50% | 40% |

*[1]: aziridine resin (ICI);
*[2]: polybutyl titanate

The analogous evaluation led to the following values:

| | Unit | Example 2 | Example 3 | Example 4 | Example 5 |
|---|---|---|---|---|---|
| Thickness of the polyurethane film | $\mu$m | 25 | 25 | 25 | 25 |
| Thickness of the adhesive film | $\mu$m | 30 | 25 | 45 | 60 |
| WVP$_{\text{pressure-sensitive adhesive film, inverted cup}}$ | g·m$^{-2}$·24 h$^{-1}$ | 70300 | 58300 | 65200 | 40300 |
| Adhesive strength AFERA 4001 | N/25 mm | 4.8 | 5.2 | 5.5 | 5.8 |
| Adhesive strength polyurethane skin model subjective evaluation, normed at a standard of 100% | N/25 mm | 5.2 | 4.9 | 6.5 | 4.8 |
| dry | % | 109 | 115 | 115 | 120 |
| moist | % | 180 | 120 | 222 | 140 |
| wet | % | 253 | 190 | 302 | 195 |

What is claimed is:

1. A medicinal pressure-sensitive adhesive which adheres to both dry and wet skin comprising a mixture of:
   (a) 20 to 50 wt-% of a hydrophilic (meth)acrylate copolymer containing tertiary amino groups;
   (b) 20 to 50 wt-% of a hydrophobic (meth)acrylate copolymer containing carboxyl groups;
   (c) 10 to 40 wt-% of one or more mono- or di-carboxylic acids;
   (d) 0 to 10 wt-% of a polyol; and
   (e) 0.02 to 0.5 wt-% of a cross-linking agent reacting with at least one copolymer, whereby the sum of components a to e equals 100 wt-%, with a water-vapor permeability of greater than or equal to 30,000 g·m$^{-2}$·24 h$^{-1}$, measured on a pressure-sensitive adhesive film with a thickness of 40 $\mu$m.

2. The medicinal pressure-sensitive adhesive of claim 1 wherein the hydrophilic copolymer contains dimethylaminoethyl groups.

3. The medicinal pressure-sensitive adhesive of claim 1 wherein the hydrophobic copolymer contains n-butyl acetate monomer units.

4. The medicinal pressure-sensitive adhesive of claim 1 wherein the number of C-atoms in the dicarboxylic acids is an even number and lies between 12 and 16.

5. The medicinal pressure-sensitive adhesive of claim 1 wherein the number of C-atoms in the dicarboxylic acids is an even number and lies between 6 and 10.

6. The medicinal pressure-sensitive adhesive of claim 1 wherein the cross-linking agent is a metal chelate, a metal acid ester, a blocked polyisocyanate, an epoxide resin, an aziridine resin or a triazine resin.

7. The medicinal pressure-sensitive adhesive of claim 1 wherein the polyol is glycerin.

8. A medicinal plaster with good skin adhesion comprising a pressure-sensitive adhesive of claim 1.

9. The medicinal plaster of claim 8 further comprising textile sheet materials, films, foams or paper as carrier materials.

10. The medicinal plaster of claim 9 in sterilized form.

11. A wound plaster comprising the medicinal plaster of claim 8.

12. A securing plaster comprising the medicinal plaster of claim 8.

13. An occlusive dressing for the transdermal application of active substances comprising the medicinal plaster of claim 8.

14. The medicinal plaster of claim 8 in sterilized form.

15. A method of making an occlusive dressing which is insensitive to wetness comprising including the medicinal pressure-sensitive adhesive of claim 1 in the occlusive dressing.

* * * * *